United States Patent
Zaeuner et al.

(10) Patent No.: US 10,719,986 B2
(45) Date of Patent: Jul. 21, 2020

(54) METHOD AND SYSTEM FOR VIRTUAL PERCUTANEOUS VALVE IMPLANTATION

(75) Inventors: Dominik Zaeuner, Gilching (DE); Razvan Ioan Ionasec, Lawrenceville, NJ (US); Bogdan Georgescu, Plainsboro, NJ (US); Yefeng Zheng, Dayton, OH (US); Dorin Comaniciu, Princeton Junction, NJ (US); Ingmar Voigt, Erlangen (DE); Jan Boese, Eckental (DE)

(73) Assignee: Siemens Healthcare GmbH, Erlangen (DE)

( * ) Notice: Subject to any disclaimer, the term of this patent is extended or adjusted under 35 U.S.C. 154(b) by 1861 days.

(21) Appl. No.: 12/975,714

(22) Filed: Dec. 22, 2010

(65) Prior Publication Data

US 2011/0153286 A1 Jun. 23, 2011

Related U.S. Application Data

(60) Provisional application No. 61/289,183, filed on Dec. 22, 2009.

(51) Int. Cl.
*G06T 17/00* (2006.01)
*G06T 19/00* (2011.01)
*G16H 50/50* (2018.01)
*G06F 19/00* (2018.01)

(52) U.S. Cl.
CPC ............. *G06T 19/00* (2013.01); *G06T 17/00* (2013.01); *G16H 50/50* (2018.01); *G06F 19/321* (2013.01); *G06T 2219/2004* (2013.01)

(58) Field of Classification Search
CPC . A61N 1/18; G09B 23/28; G09G 7/48; A61B 5/05; G06F 19/3437
USPC .............. 600/407; 607/14; 703/11, 7; 705/2; 434/262, 267, 272
See application file for complete search history.

(56) References Cited

U.S. PATENT DOCUMENTS

| | | | |
|---|---|---|---|
| 7,840,393 B1 * | 11/2010 | Whirley et al. | 703/7 |
| 2004/0153128 A1 * | 8/2004 | Suresh et al. | 607/14 |
| 2005/0148850 A1 * | 7/2005 | Lahm et al. | 600/407 |
| 2005/0202384 A1 * | 9/2005 | DiCuccio et al. | 434/262 |

(Continued)

OTHER PUBLICATIONS

Volumetric Medical Images Segmentation Using Shape Constrained Deformable Models by J. Montagnat and H. Delingette in Proceedings of the First Joint Conference CVRMed-MRCAS'97, vol. 1205 of Lecture Notes in Computer Science, pp. 13-22, Mar. 1997. (http://www-sop.inria.fr/members/Herve.Delingette/biblio2.html).*

(Continued)

*Primary Examiner* — Bruk A Gebremichael (57) ABSTRACT

A method and system for virtual percutaneous valve implantation is disclosed. A patient-specific anatomical model of a heart valve is estimated based on 3D cardiac medical image data and an implant model representing a valve implant is virtually deployed into the patient-specific anatomical model of the heart valve. A library of implant models, each modeling geometrical properties of a corresponding valve implant, is maintained. The implant models maintained in the library are virtually deployed into the patient specific anatomical model of the heart valve to select an implant type and size and deployment location and orientation for percutaneous valve implantation.

19 Claims, 9 Drawing Sheets

(56) References Cited

U.S. PATENT DOCUMENTS

| | | |
|---|---|---|
| 2006/0098007 A1* | 5/2006 | Rouet .................... G06T 17/20 345/419 |
| 2007/0208550 A1* | 9/2007 | Cao et al. ....................... 703/11 |
| 2009/0281609 A1 | 11/2009 | Benichou et al. |
| 2009/0306500 A1 | 12/2009 | Rahn et al. |
| 2010/0106475 A1* | 4/2010 | Smith et al. ................... 703/11 |
| 2010/0191541 A1* | 7/2010 | Prokoski .......................... 705/2 |
| 2010/0239147 A1 | 9/2010 | Vitanovski et al. |
| 2012/0207365 A1* | 8/2012 | Verstraeten et al. .......... 382/128 |

OTHER PUBLICATIONS

Marching Cubes: A High Resolution 3D Surface Contruction Algorithm by William E Lorensen and Harvey E. Cline, Computer Graphis, vol. 21, No. 4, Jul. 1987.*

Volumetric Medical Images Segmentation Using Shape Constrained Deformable Models by J. Montagnat and H. Delingette in Proceedings of the First Joint Conference CVRMed-MRCAS'97, vol. 1205 of Lecture Notes in Computer Science, pp. 13-22, Mar. 1997.*

A partitioned strongly coupled fluid-structure interaction method to model heart valve dynamics by J. Vierendeels, K. Dumont and P.R. Verdonk received Sep. 10, 2005.*

Ionasec, Razvan Ioan, et al., "Patient-Specific Modeling and Quantification of the Aortic and Mitral Valves from 4D Cardiac CT and TEE", Submitted to IEEE Transactions on Medical Imaging, (Sep. 2010), 17 pages.

Ionasec, Razvan Ioan, et al., "Personalized Modeling and Assessment of the Aortic-Mitral Coupling from 4D TEE and CT", In International Conference on Medical Image Computing and Computer-Assisted Intervention (MICCIA), London, USA (Sep. 2009), 9 pages.

* cited by examiner

Input:
  - Patient-specific model of aortic valve and aorta ascendenx
  - implant placement position and orientation Output: Deployed Implant
Execute:

602 — - create computational mesh and stent mesh with constant radius of 1 mm at manually selected placement position, oriented along the aortic root centerline
  - repeat:
604 —   • for each point $p_j^n$ on the *computational mesh*, calculate $f_{reg}(p_j^n)$, $f_{angle}(p_j^n)$, $f_{length}(p_j^n)$, $f_{arc}(p_j^n)$ and $f_{act}(p_j^n)$
606 —   • for each $p_j^n$, compute $p_j^{n+1}$ according to Eq. 1
608 —   • if mean point displacement on the *stent mesh* $<e$, convergence achieved; stop execution

METHOD AND SYSTEM FOR VIRTUAL PERCUTANEOUS VALVE IMPLANTATION

This application claims the benefit of U.S. Provisional Application No. 61/289,183, filed Dec. 22, 2009 and U.S. Provisional Application No. 61/316,447, filed Mar. 23, 2010, the disclosures of which is are herein incorporated by reference.

BACKGROUND OF THE INVENTION

The present invention relates to percutaneous valve implantation, and more particularly, to virtual percutaneous valve implantation using medical images.

Valvular heart disease (VHD) is a cardiac disorder that affects a large number of patients and often requires elaborate diagnostic procedures, intervention, and long-term management. Traditionally, heart valve replacement has been performed surgically on an open heart, with associated risks including, high mortality, incidence of neurological damage, stroke, and repeated valve replacement. However, minimally invasive procedures for the valve replacement are less traumatic and reduce the risks associated with valve replacement. Percutaneous valve implantation offers a less invasive alternative to open heart surgery for patients in need of heart valve replacement, in which a prosthetic implant is delivered through a catheter. Examples of percutaneous valve implantation include percutaneous aortic valve implantation (PAVI) and percutaneous pulmonary valve implantation (PPVI).

In percutaneous valve implantation, prosthetic implants are delivered through catheters using transvenous, transarterial, or transapical techniques, while clinicians do not have a direct view of and access to the affected valve and surrounding anatomies. Accordingly, critical decisions, such as type of procedure, implant type and size, deployment location and timing, and treatment assessment, are typically based on imaging techniques. A misplaced implant can block the coronary ostia and induce a life threatening ischemic condition. Suboptimal deployment location can result in poor hemodynamic performance with severe paravalvular leakages and/or high gradients and suboptimal effective orifice. Incorrect implant sizing may require a re-operation and may damage the vessel tissue and cause catastrophic events, such as arterial dissection or rupture. Accordingly, improved techniques for percutaneous valve implantation planning, procedure guidance, and outcome assessment are desirable.

BRIEF SUMMARY OF THE INVENTION

The present invention provides a method and system of virtual valve implantation for planning, guidance, and assessment of percutaneous valve implantation techniques. Embodiments of the present invention can be used for various types of valve implantation, such as percutaneous aortic valve implantation (PAVI) and percutaneous pulmonary valve implantation (PPVI). Embodiments of the present invention can be used pre-operatively for identification of optimal device type, size and deployment location and for treatment outcome prediction. Embodiments of the present invention can alternatively be used post-operatively quantitative implant assessment.

In one embodiment of the present invention, a patient-specific anatomical model of a heart valve is estimated based on 3D cardiac medical image data. An implant model representing a valve implant is virtually deployed into the patient-specific anatomical model of the heart valve. A library of implant models, each modeling geometrical properties of a corresponding valve implant, can be maintained. The implant models maintained in the library can be virtually deployed into the patient specific anatomical model of the heart valve to select one of the implant models for use in a percutaneous valve implantation procedure.

These and other advantages of the invention will be apparent to those of ordinary skill in the art by reference to the following detailed description and the accompanying drawings.

DETAILED DESCRIPTION

The present invention relates to a virtual valve implantation framework for modeling and quantitative evaluation of a percutaneous valve implantation procedure. Embodiments of the present invention are described herein to give a visual understanding of the virtual valve implantation method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Embodiments of the present invention are described herein as using 3D or 4D CT data to model patient-specific anatomy. It is to be understood that the present invention is not limited to CT, but can be applied to other medical imaging techniques, such as magnetic resonance imaging (MRI), echocardiography, etc.

According to various embodiments of the present invention, the virtual valve replacement framework described herein can be utilized in both a pre-operative framework and a post-operative framework. In the pre-operative framework, pre-operative medical images, such as cardiac CT images, are acquired, a patient-specific anatomical model of the valve is estimated, and in-silico valve implantation under various interventional procedure conditions is performed for identification of an optimal device type of the prosthetic valve, size and deployment location, and treatment outcome prediction. In the post-operative workflow, post-operative medical images, such as cardiac CT images, are acquired, a patient-specific anatomical model is estimated, and patient-specific deployed device estimation is performed for quantitative implant assessment.

Figure 1:
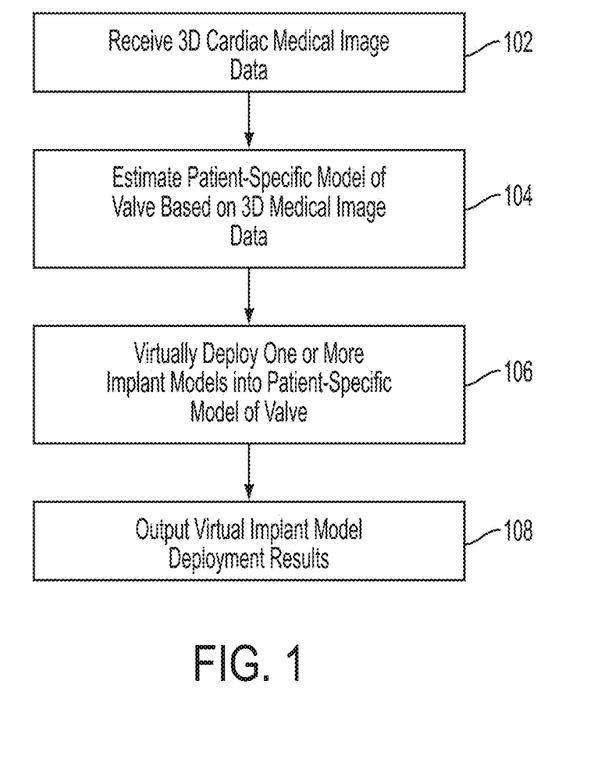
FIG. 1 illustrates a method of virtual valve implantation according to an embodiment of the present invention.

FIG. 1 illustrates a method of virtual valve implantation according to an embodiment of the present invention. The method of FIG. 1 transforms 3D medical image data representing a patient's anatomy to generate a patient-specific anatomical model and uses the anatomical model to virtually simulate the implantation of one or more implants (also referred to herein as "stents"). As described herein, the method of FIG. 1 is applied to virtual percutaneous aortic valve implantation (PAVI). It is to be understood that this method may be similarly applied for virtual implantation of other heart valves including virtual percutaneous pulmonary valve implantation (PPVI).

Referring to FIG. 1, at step 102, 3D cardiac medical image data is received. For example, the 3D medical image data may be 3D cardiac CT data, but the present invention is no limited thereto. According to various embodiments, the 3D medical image data may include image data may be obtained from one or more of the following imaging modalities: CT, Dyna CT—C-arm 3D reconstruction, MRI, or 3D echocardiography. The medical image data may include 4D cardiac medical image data, that is, a sequence of 3D medical images taken over a period of time. It is possible that the image data can be received directly from an image acquisition device, such as a CT scanning device, in real time as the image data is acquired by the image acquisition device. It is also possible that the image data can be received by loading image data stored in a memory or storage of a computer system, or some other computer readable medium At step 104, a patient-specific model of the aortic valve is estimated based on the 3D cardiac medical image data. According to an advantageous implementation, an anatomical model of the aortic valve and ascending aorta is estimated from the medical image data.

Figure 2:
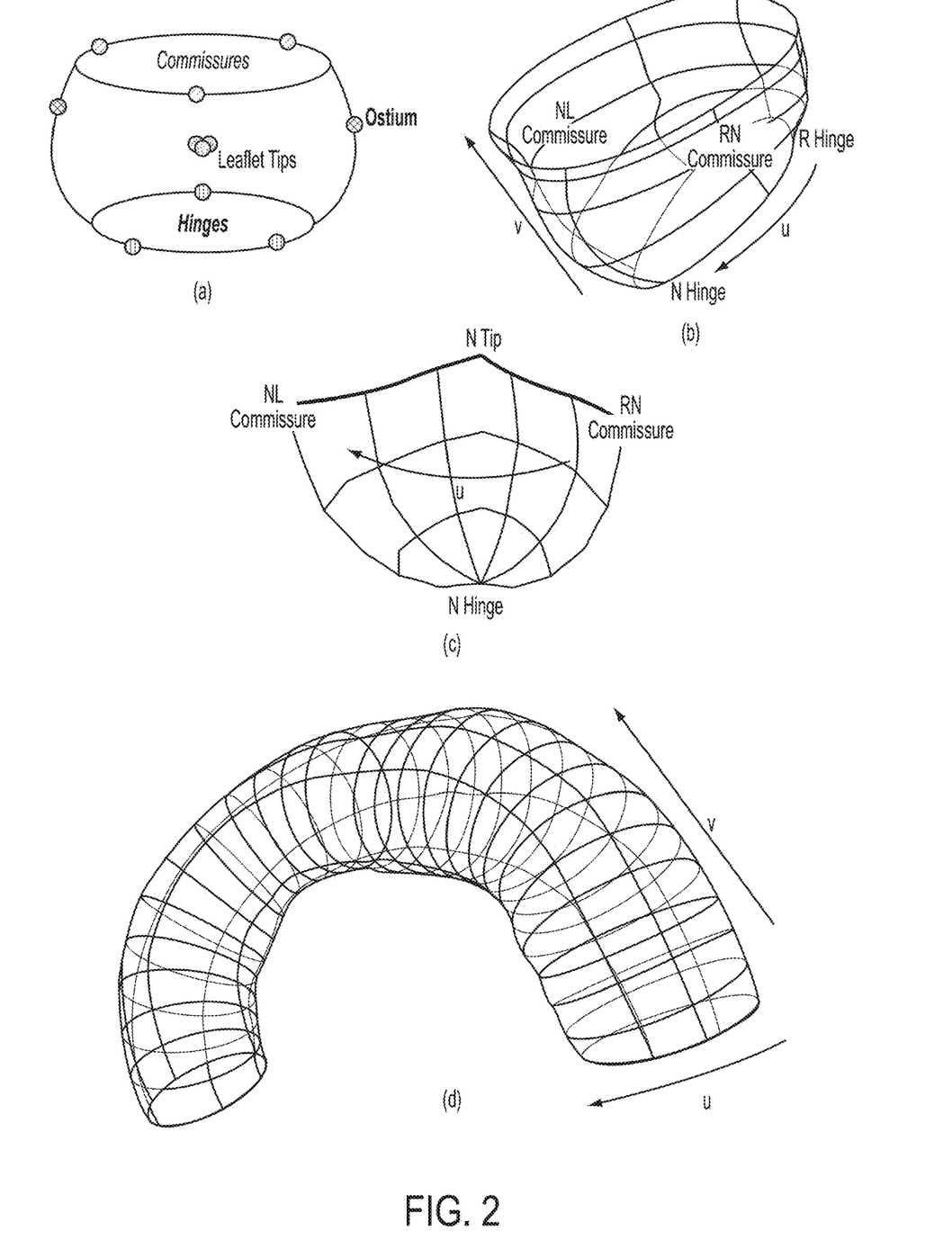
FIG. 2 illustrates an aortic valve and ascending aortic root model.

FIG. 2 illustrates an aortic valve and ascending aortic root model. As illustrated in FIG. 2, image (a) shows a schematic view of the aortic valve including 11 anatomical landmarks (3 hinges, 3, leaflet tips, 3 commissures, and 2 ostia). Image (b) shows a point distribution model of the aortic root. Image (c) shows a model of an aortic leaflet. Image (d) shows an ascending aortic root model. The aortic root provides the supporting structures for the leaflets oaf the aortic valve and forms the bridge between the left ventricle and the ascending aorta. The root extends from the basal attachments of the leaflets, defined by the L (left), R (right), and N (none) hinges to the sinutubular junction. The L, R, and N aortic leaflets are attached to the root on semilunar structures. Valve leaflets can be thought of as shirt pockets, with one edge stitched to the shirt and one edge free of attachment, where its center marked by the respective L, R, or N leaflet tip. These attachment structures interlink at the level of the sinutubular junction forming the LR, RN, and NL commissures. The model described herein represents the complete anatomy of the aortic valve and ascending aorta, which includes the aortic root, L, R, and N aortic leaflets, ascending aorta, and 11 anatomical landmarks The 11 anatomical landmarks are represented by 3D points in Euclidean space. The landmarks represented in the model are the L, R, and N hinges, LR, RN, and NK commissures, L, R, and N leaflet tips, and L and R coronary ostia. The aortic root is constrained by the commissures, hinges, and ostia, and represented as a tubular surface mesh. The mesh is parameterized along the aortic circumferential and ascending directions, u and v, respectively, and includes 36×10 vertices in an exemplary implementation. The L, R, and N aortic leaflets can be modeled as hyperbolic paraboloids on a grid of 11×7 vertices. Each leaflet is constrained by one hinge, two commissures and one leaflet tip. For example, as shown in image (c) of FIG. 2, the N leaflet is constrained by the N hinge, the NL and RN commissures, and the N leaflet tip. The ascending aorta emerges from the aortic root and incorporates a variable length. The anatomy includes a fixed number of circumferential coordinates (e.g., u=36) and a variable number of coordinates along the ascending direction v. Accordingly, a ring is formed by the circumferential coordinates at each ascending direction coordinate. The first ring is located at the commissures.

According to an embodiment of the present invention, the patient-specific parameters of the aortic valve and ascending aorta model described above can be estimated from the 3D medical image data using a robust learning-based algorithm. Such a learning-based algorithm for estimating patient-specific parameters is described in detail in Ionasec, et al., "Modeling and Assessment of the Aortic-Mitral Valve Coupling from 4D Tee and CT", *International Conference on Medical Image Computing and Computer-Assisted Intervention (MICCAI)*, September 2009, which is incorporated herein by reference. The a posteriori probability p(M|I) of the model M given the image I, is hierarchically estimated within the Marginal Space Learning (MSL) Framework. The MSL framework is described in detail in U.S. Published Patent Application No. 2009/0304251. Detectors are successively trained using a Probabilistic Boosting Tree (PBT) with Haar and Steerable features, and consequently applied to estimate the anatomical landmarks and structures for a particular patient from the received 3D medical image data.

Figure 3:
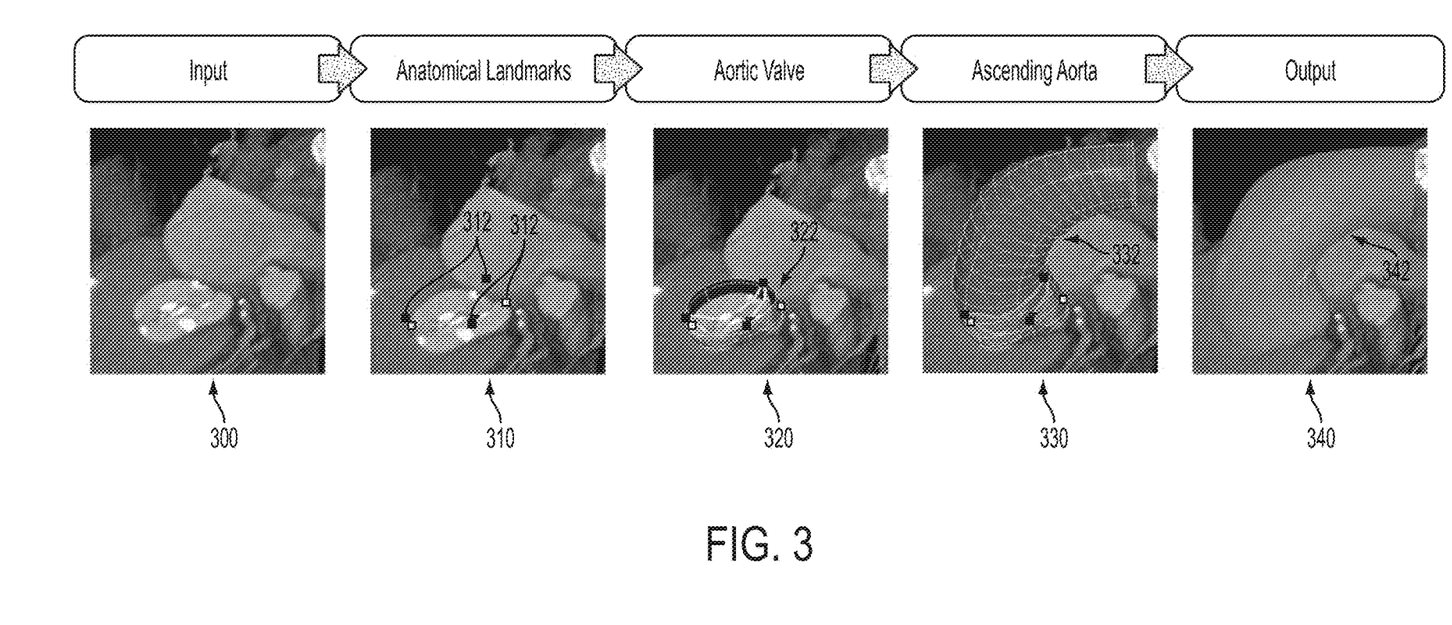
FIG. 3 illustrates estimation of a patient specific aortic valve and ascending aorta model.

FIG. 3 illustrates the estimation of a patient specific aortic valve and ascending aorta model. As illustrated in FIG. 3, image 300 is an input CT image. Image 310 shows the anatomical landmarks 302 detected in the input CT image. Image 320 shows the patient-specific aortic valve model 322 defined by the anatomical landmarks. Image 330 shows the estimated ascending aorta 330. Image 340 shows the output patient-specific aortic valve and ascending aorta model 342.

Returning to FIG. 1, at step 106, one or more implant models are virtually deployed into the patient-specific model of the valve. A library of virtual devices/implant models is maintained based on manufacturers' descriptions to incorporate realistic geometrical and bio-mechanical properties of various physical devices/implants. The device library can be easily extended by creating implant models representing any future devices. Each implant model includes two parts: a geometric representation, or "stent mesh", which precisely mimics the exact geometry of the device, and a second superimposed 2-simplex mesh, or "computational mesh", which is used for accurate and efficient computation and to guide the expanding deformation of the implant model.

Figure 4:
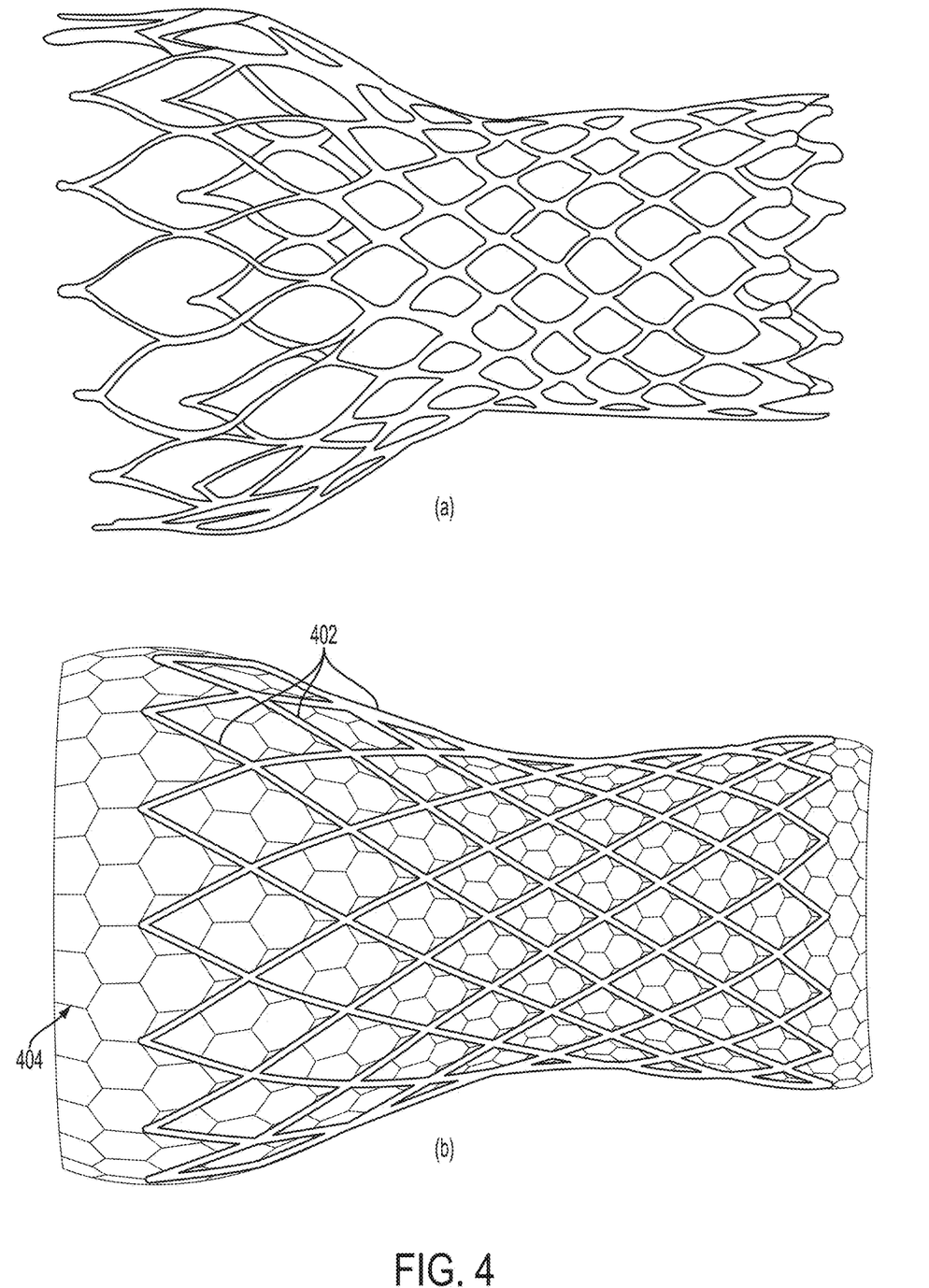
FIG. 4 illustrates an implant model representing an exemplary valve implant.

FIG. 4 illustrates an implant model representing an exemplary valve implant. As illustrated in FIG. 4, image (a) shows a CoreValve implant. The CoreValve implant of image (a) is a model of the CoreValve Revalving System by Medtronic, such as models CRS-P3-640 and CRS-P3-943. These two CoreValve models have respective lengths of 53 and 55 mm, respective diameters at the inflow level of 26 and 29 mm, respective diameters at the middle level of 22 and 24 mm, and respective diameters at the outflow level of 40 and 43 mm. Image (b) of FIG. 4 depicts the topological relationship between the computational mesh and the stent mesh representing the CoreValve implant of image (a). As shown in image (b), the stent mesh 402 is composed of struts connecting a subset of points of the computational mesh 404. In order to infer the geometrical properties of the stent model, various dimensions can be measured from stereolithographic scans of the modeled implants. These geometrical properties are the strut lengths, the characteristic angles in each cell, and the device's circumferences at each level, where each level is defined by the strut joints.

In order to simulate valve replacement under various conditions, different implant models can be selected from the library and virtually deployed under different parameters, into the extracted patient-specific model. In can be noted, that after step 104 of the method of FIG. 1, the initial image data may no longer be needed, as the virtual implant deployment is dependent on the extract patient-specific model, but independent of the underlying image data. The expansion of a selected implant model is modeled by balancing external and internal forces as encountered in the actual procedure, using iterative optimization methods. According to an advantageous implementation, the expansion of the implant can be described by a finite difference discretization of a second order differential equation:

$$p_i^{n+1} = p_i^n + (1-\gamma)(p_i^n + p_i^{n-1}) + f_{int}(p_i^n) + f_{ext}(p_i^n) + f_{reg}(p_i^n) \quad (1)$$

where $p_i$ is a point on the computational mesh, n is the iteration number, $f_{ext}$, $f_{int}$, and $f_{reg}$ are the external, internal, and regularizing forces, respectively, and $\gamma$ is a weighting parameter. The internal forces $f_{int}(p_i^n) = f_{length}(p_i^n) + f_{angle}(p_i^n) + f_{circ}(p_i^n)$ model the intrinsic properties of the stent and enforce deformation along its surface normals and long axis, as the device is self-expandable. Hence, the internal forces are parameterized by strut lengths, characteristic angles, and device circumferences, which were measured from the expanded template. Accordingly, these forces are adapted, such that the implant attempts to achieve the targeted dimensions, and the forces induce different expanding pressures at different levels. In particular, $f_{circ}(p_i^n) = n_i(c_k - \Sigma \forall i \in N_k \|p_j^n - p_{j+1}^n\|)/2\pi$ pushes the points $p_i^n \in N_k$ along the surface normal $n_i$ to satisfy the reference circumference $c_k$ of the stent shape, where $N_k$ is the set of strut joints at a level k. It is important to note that $f_{circ}$ does not enforce the stent diameter directly, but the stent circumference instead in order to account for expansion into arbitrary shaped vessel geometries, which typically have non-circular cross-sections. $f_{length}$ and $f_{angle}$ enforce the strut lengths and characteristic angles observed in the expanded shape. The external forces $f_{ext}(p_i)$ model the interaction of the stent and the aortic valve and aorta tissue, and guide the implant deformation by balancing the internal device forces $f_{ext}(p_i) = -n_i(n_i \cdot f_{int}(p_i))(\|p_i^n - c_k\| l \| v - c_k\|)$ with centroid $c_k$ at level k and the intersection point v of the normal and the vessel surface. The regularizing forces $f_{reg}$ are solely defined on the computational mesh to provide smoothness. It is to be understood that the method described herein applies to self-expanding implants, which inherently exercise forces of minor amplitudes onto the surrounding vessel tissue, and the resulting minor deformations can be neglected.

Figure 5:
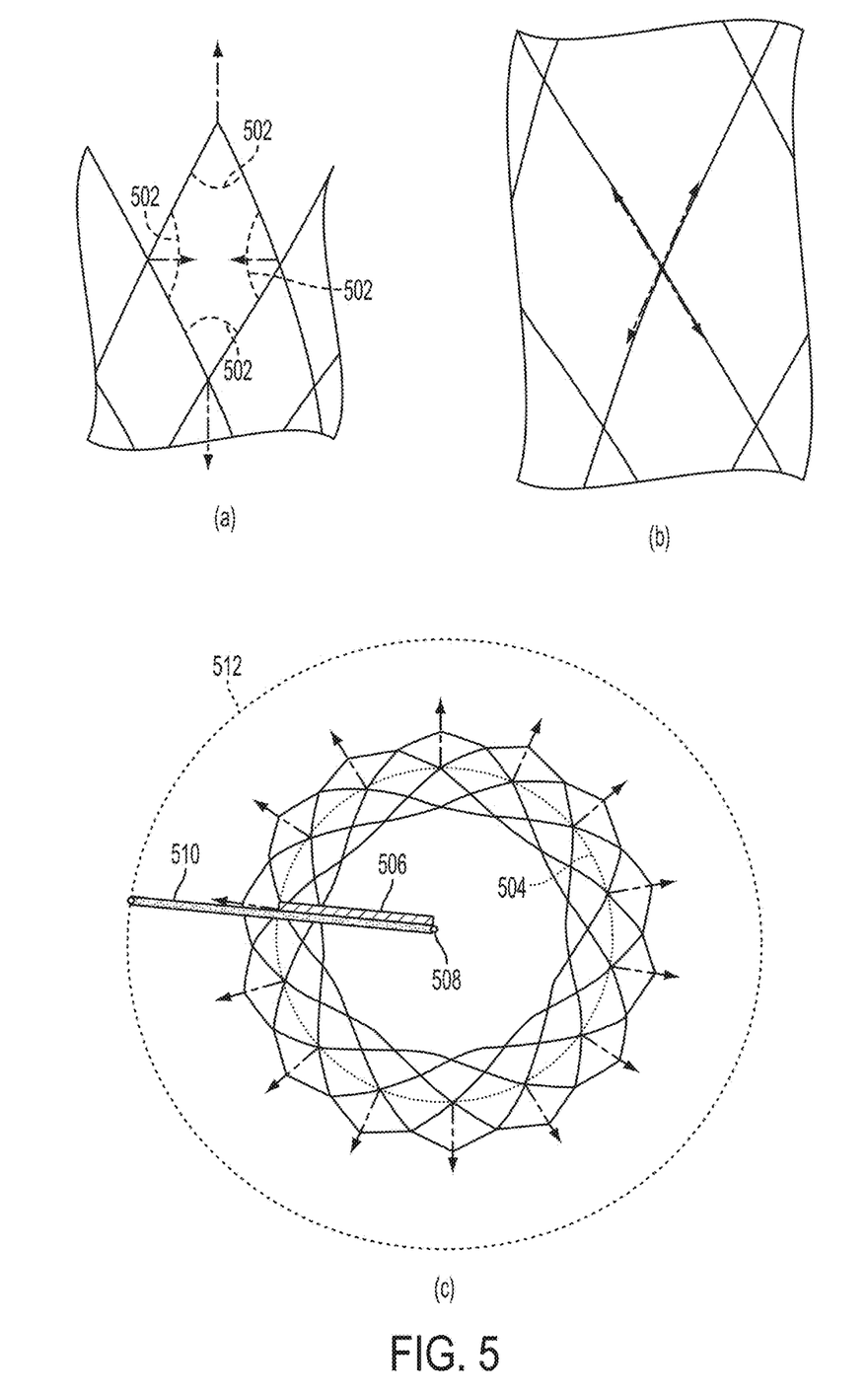
FIG. 5 illustrates forces acting on an implant model during virtual deployment.

FIG. 5 illustrates the forces acting on the implant model during virtual deployment, which were described above. As illustrated in FIG. 5, the arrows of image (a) represent the $f_{angle}$, which enforces characteristic angles 502 at the strut joints. The arrows of image (b) represent $f_{length}$, which maintains the strut lengths. Image (c) shows a short axis cross-section of the stent mesh. The arrows of image (c) represent $f_{circ}$, which enforces the circumference 504, while $f_{ext}$ dampens and eliminates all of the forces acting along the stent mesh normal weighted by a ratio of the distance 506 from the strut joint the stent centroid 508 and the distance 510 from the vessel wall 512 to the stent centroid 508.

Figure 6:
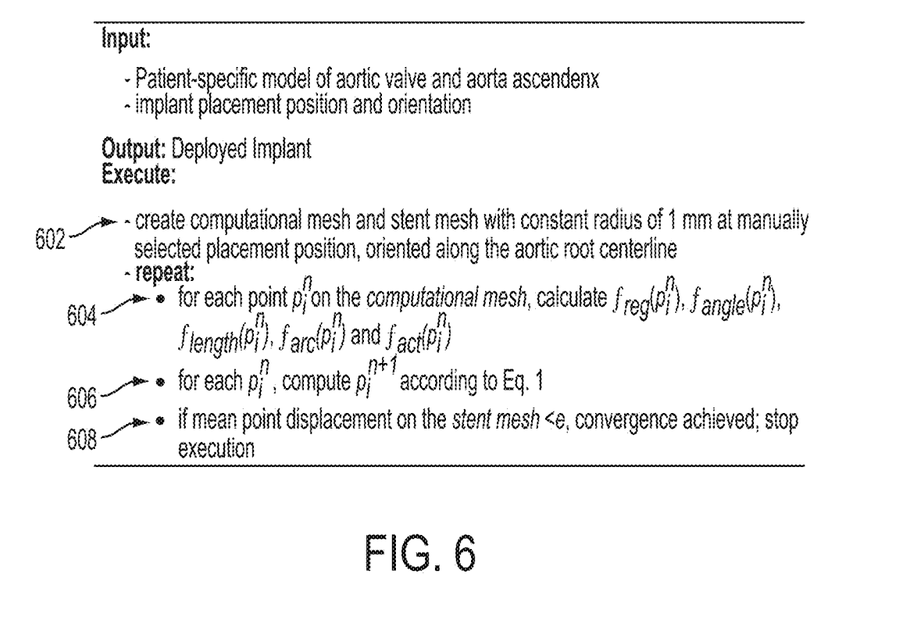
FIG. 6 is pseudo code illustrating an algorithm for implementing virtual deployment of an implant model according to an embodiment of the present invention.

FIG. 6 is pseudo code illustrating an algorithm for implementing virtual deployment of an implant model according to an embodiment of the present invention. It is to be understood that the algorithm of FIG. 6 can be performed by a processor to implement step 106 of FIG. 1. The algorithm of FIG. 6 receives as input the patient-specific model of the aortic valve and ascending aorta and an implant placement position and orientation and outputs a virtually deployed implant. At 602, a computational mesh and a stent mesh corresponding to the implant model to be deployed is created at the placement position and oriented along the aortic root centerline. The radius of the computational mesh and stent mesh is initialized, for example at 1 mm. At step 604, for each point $p_i^n$ on the computational mesh $f_{reg}(p_i^n)$, $f_{angle}(p_i^n)$, $f_{length}(p_i^n)$, $f_{circ}(p_i^n)$, and $f_{ext}(p_i^n)$ are calculated, as described above. At step 606, for each point $p_i^n$, $p_i^{n+1}$ is calculated according to Equation (1). At step 608, the mean point displacement on the stent mesh is determined and if the mean point displacement on the stent mesh is less than a threshold $\varepsilon$, convergence is achieved and the algorithm stops. If the mean point displacement on the stent mesh is not less than the threshold $\varepsilon$, steps 604, 606, and 608 are repeated until convergence is achieved.

Returning to FIG. 1, at step 108, the virtual implant model deployment results are output. The virtual implant deployment results can provide quantitative and qualitative information used in planning and performing the percutaneous valve implantation. For example, using the virtual-deployment framework various implants can be tested and compared to select the best implant and implant size. Further, the virtual implantation can provide an optimal position and orientation for the selected implant with respect to the patient-specific model. Quantitatively, the forces that hold the stent to the wall can be calculated after virtual deployment. Hemodynamic performance of the implant can be predicted by quantifying paravalvular leakages, valve insufficiency, and effective orifice and systolic gradients across the aortic prosthesis. The virtual valve deployment results may be output as a visualization of the implant model in the patient-specific valve model. By simulating the procedure visually, physicians can predict complications of the procedure and minimize risks of the procedure. In addition, treatment options can be optimized by testing different hypotheses to select the best deployment options.

According to an advantageous embodiment, the virtual valve replacement framework allows for accurate navigation during the actual intervention. The optimal deployment position and orientation determined during the virtual planning stage can be superimposed on top of live fluoroscopic images and tracked during the actual procedure. Clinicians can guide their deployment device to exactly match the virtual deployment point and proceed with the deployment at the optimal location determined using the virtual valve replacement.

Figure 7:
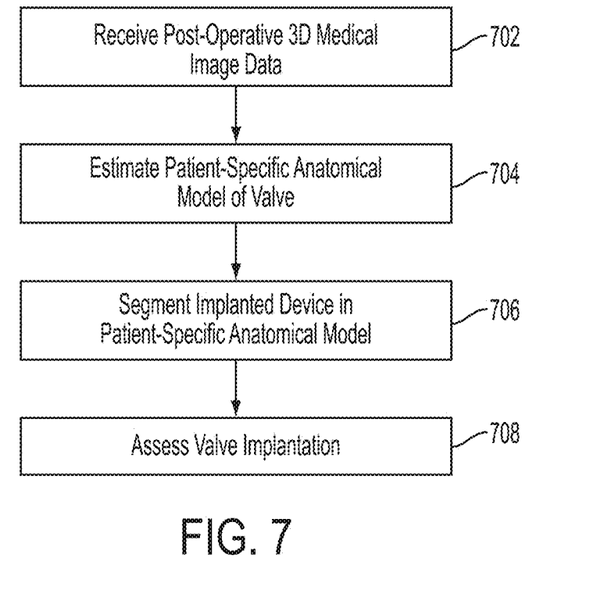
FIG. 7 illustrates a method of post-operative assessment of a percutaneous valve implantation procedure according to an embodiment of the present invention.

Furthermore, a post-operative workflow can be performed for assessment of a percutaneous valve implantation procedure. FIG. 7 illustrates a method of post-operative assessment of a percutaneous valve implantation procedure according to an embodiment of the present invention. Referring to FIG. 7, at step 702, post-operative 3D medical imaging data is received. For example, a post-operative 3D cardiac CT volume can be received.

At step 704, a patient-specific anatomical model of the valve is estimated from the post-operative 3D medical imaging data. The estimation of the patient-specific anatomical model in step 704 can be performed as described above with respect to step 104 of FIG. 1.

At step 706, the implanted device is segmented in the patient-specific anatomical model. In an exemplary implementation, the implanted device may be segmented by fitting the corresponding implant model from the library to the patient-specific anatomical model. This procedure can be initialized by a user click at a location of the implanted device in the patient-specific anatomical model.

At step 708, the valve implantation procedure is assessed based on the segmented device. In one embodiment, the quality of the implantation can be assessed by calculating the distances of the segmented device to various anatomical landmarks of the patient-specific anatomical model. These distances can be compared with target distances corresponding to each anatomical landmark. The target distances can be based on the pro-operative virtual (in-silica) valve implantation performed using the method of FIG. 1.

According to another embodiment, the post-operative segmented device (implant) can be used as a ground truth to validate the prediction generated by the pre-operative virtual deployment of the implant. In the post-operative volume, the ground truth implant can be manually placed and fit to the imaged stent, which is well visible in the post-operative image data, using a semi-automatic method based on the thin-plate-spline transformation. The ground truth can be compared to a corresponding virtually deployed implant to validate accuracy of the virtually deployed implant. The ground truth and corresponding virtually deployed implant can be compared by visualizing the ground truth and virtually deployed implant. The ground truth and corresponding virtually deployed implant can also be compared on the basis of internal precision, by comparing their shapes in isolation via symmetric point-to-point distance, and on the basis of external precision (e.g., using distances to anatomic landmarks).

Figure 8:
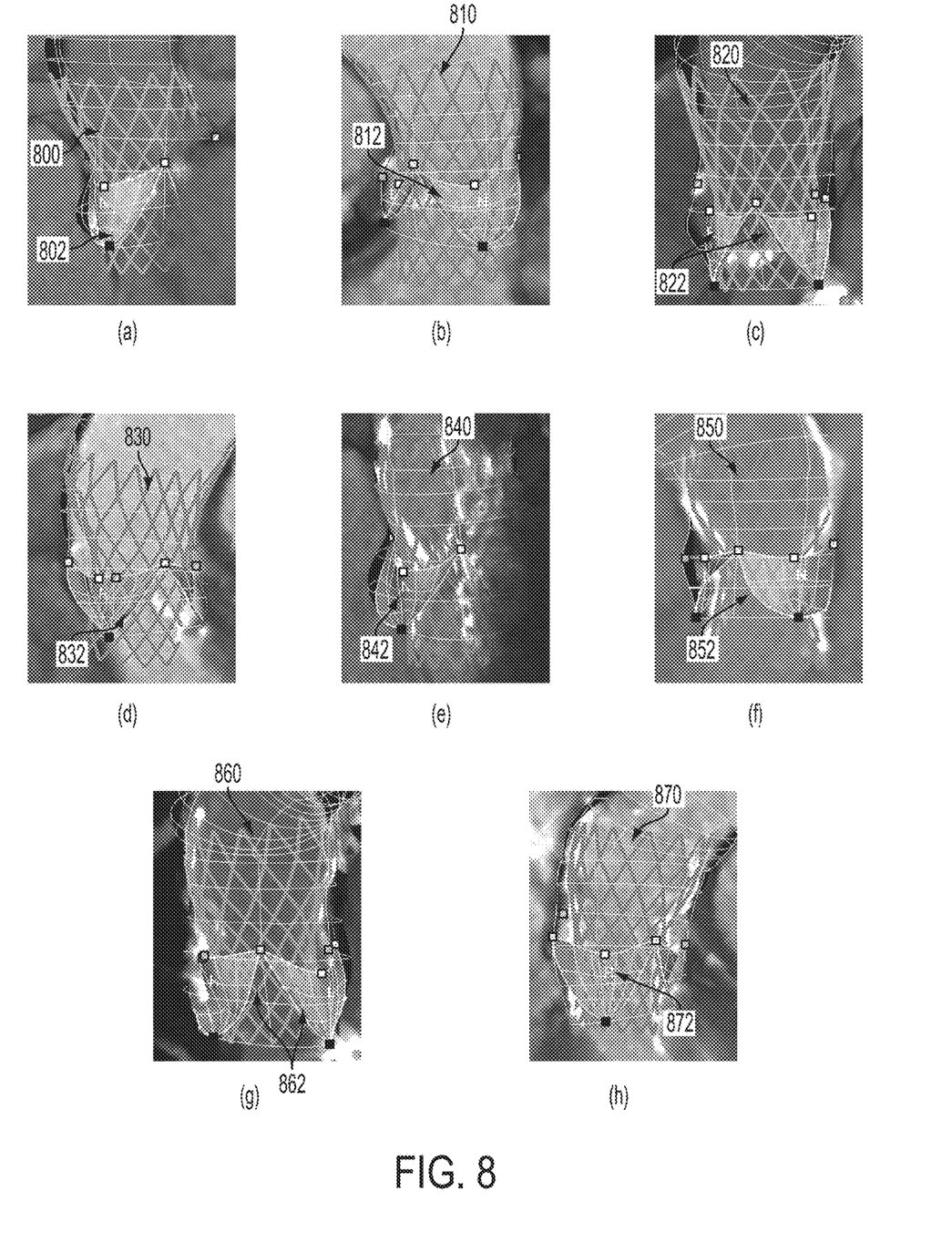
FIG. 8 illustrates exemplary pre-operative virtual implant deployment results and corresponding post-operative ground truths.

FIG. 8 illustrates exemplary pre-operative virtual implant deployment results and corresponding post-operative ground truths. Images (a), (b), (c), and (d) show virtually deployed implant models 800, 810, 820, and 830 overlayed with the estimated patient-specific anatomical valve models 802, 812, 822, and 832, respectively. Virtually deployed implant models 800, 810, 820, and 830 were detected using the methods illustrated in FIGS. 1 and 6. Images (e), (f), (g), and (h) show post-operative ground truth stents 840, 850, 860, and 870 corresponding to the virtually deployed implant models 800, 810, 820, and 830, respectively. Also, as shown in images (e), (f), (g), and (h), the post-operative ground truth stents 840, 850, 860, and 807 are overlayed with estimated patient specific anatomical valve models 842, 852, 862, and 872, respectively.

Figure 9:
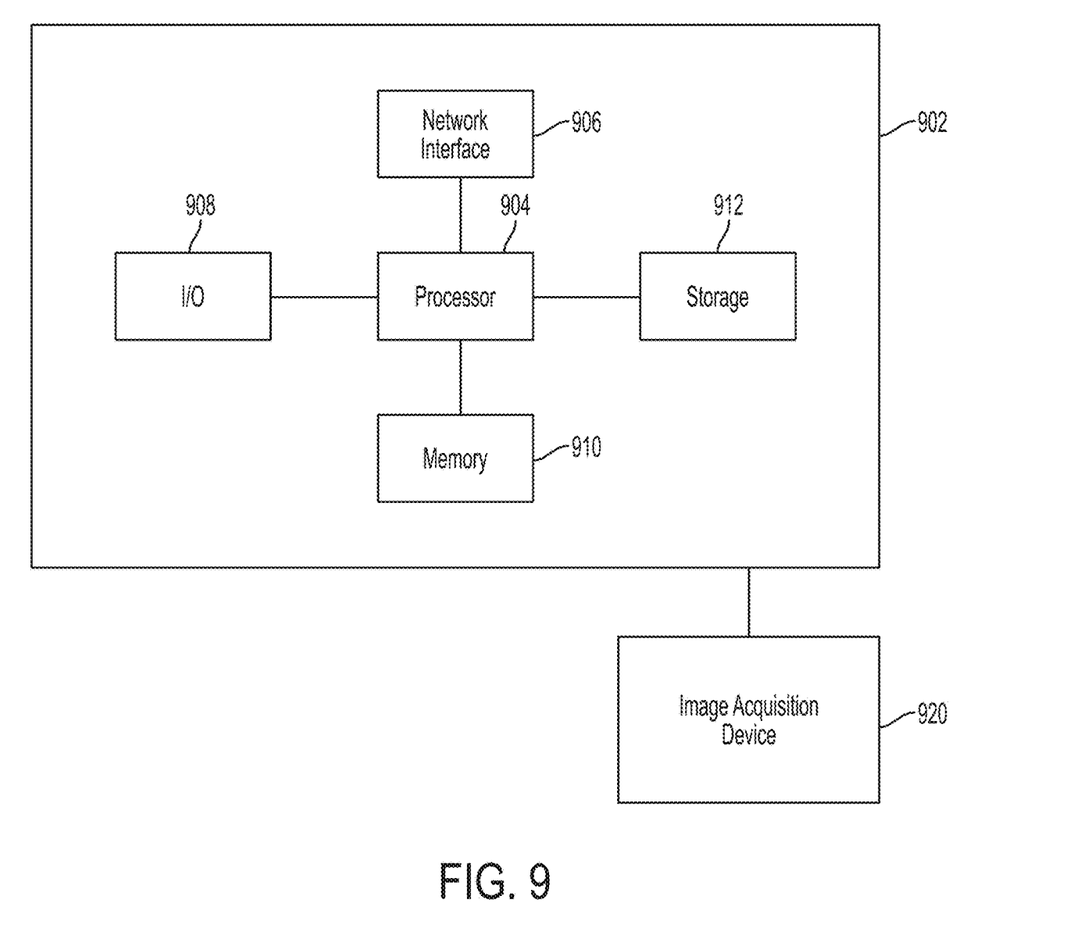
FIG. 9 is a high-level block diagram of a computer capable of implementing the present invention.

The above-described methods for virtual valve replacement (FIGS. 1 and 6) and post-operative assessment (FIG. 7) may be implemented on a computer using well-known computer processors, memory units, storage devices, computer software, and other components. A high-level block diagram of such a computer is illustrated in FIG. 9. Computer 902 contains a processor 904, which controls the overall operation of the computer 902 by executing computer program instructions which define such operation. The computer program instructions may be stored in a storage device 912 (e.g., magnetic disk) and loaded into memory 910 when execution of the computer program instructions is desired. Thus, the steps of the methods of FIGS. 1, 6, and 7 may be defined by the computer program instructions stored in the memory 910 and/or storage 912 and controlled by the processor 904 executing the computer program instructions. An image acquisition device 920, such as a CT scanning device, can be connected to the computer 902 to input image data to the computer 902. It is possible to implement the image acquisition device 920 and the computer 902 as one device. It is also possible that the image acquisition device 920 and the computer 902 communicate wirelessly through a network. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for computer-implemented simulation of percutaneous valve implantation, comprising:
   estimating a patient-specific anatomical model of a heart valve based on 3D cardiac medical image data; and
   simulating deployment of an implant model representing a valve implant into the patient-specific anatomical model of the heart valve and expansion of the implant model, wherein the implant model comprises a stent mesh that is a geometrical representation of the valve implant and a computational mesh that is a 2-simplex mesh superimposed on the stent mesh.

2. The method of claim 1, wherein said step of simulating deployment of an implant model representing a valve implant into the patient-specific anatomical model of the heart valve and expansion of the implant model comprises:
   maintaining a library of implant models, each modeling geometrical properties of a corresponding valve implant; and
   simulating deployment and expansion of each of a plurality of the implant models maintained in the library in the patient specific anatomical model of the cardiac valve to select one of the plurality of the implant models maintained in the library for a percutaneous implantation procedure.

3. The method of claim 1, wherein said step of simulating deployment of an implant model representing a valve implant into the patient-specific anatomical model of the heart valve and expansion of the implant model comprises:
   simulating expansion of the implant model by balancing external forces and internal forces using an iterative optimization method.

4. The method of claim 1, wherein said step of simulating deployment of an implant model representing a valve implant into the patient-specific anatomical model of the heart valve and expansion of the implant model comprises:

(a) calculating, for each of a plurality of points on the computational mesh, internal forces $f_{int}$, external forces $f_{ext}$, and regularizing forces $f_{reg}$;

(b) adjusting the location of each of the plurality of points on the computational mesh based on the calculated internal forces $f_{int}$, external forces $f_{ext}$, and regularizing forces $f_{reg}$;

(c) calculating a mean point displacement on the stent mesh based on the adjusted locations of the plurality of points on the computational mesh; and (d) repeating steps (a)-(c) until the mean point displacement on the stent mesh is less than a threshold.

5. The method of claim 4, wherein step (a) comprises:
calculating the internal forces $f_{int}$ by calculating a force $f_{angle}$ to enforce characteristic angles at strut joints of the implant model, a force $f_{length}$ to enforce strut lengths of the implant model, and a force $f_{circ}$ to enforce a circumference of the implant model.

6. The method of claim 1, wherein the heart valve is one of an aortic valve or a pulmonary valve.

7. The method of claim 1, further comprising:
determining a position and an orientation for implanting the valve implant based on the simulated deployment and expansion of the implant model.

8. An apparatus for simulating percutaneous valve implantation, comprising:
a processor; and
a memory storing computer program instructions, which when executed by the processor cause the processor to perform operations comprising:
estimating a patient-specific anatomical model of a heart valve based on 3D cardiac medical image data; and
simulating deployment of an implant model representing a valve implant into the patient-specific anatomical model of the heart valve and expansion of the implant model, wherein the implant model comprises a stent mesh that is a geometrical representation of the valve implant and a computational mesh that is a 2-simplex mesh superimposed on the stent mesh.

9. The apparatus of claim 8, wherein simulating deployment of an implant model representing a valve implant into the patient-specific anatomical model of the heart valve and expansion of the implant model comprises:
maintaining a library of implant models, each modeling geometrical properties of a corresponding valve implant; and
simulating deployment and expansion of each of a plurality of the implant models maintained in the library in the patient specific anatomical model of the cardiac valve to select one of the plurality of the implant models maintained in the library for a percutaneous implantation procedure.

10. The apparatus of claim 8, wherein simulating deployment of an implant model representing a valve implant into the patient-specific anatomical model of the heart valve and expansion of the implant model comprises:
simulating expansion of the implant model by balancing external forces and internal forces using an iterative optimization method.

11. The apparatus of claim 8, wherein simulating deployment of an implant model representing a valve implant into the patient-specific anatomical model of the heart valve and expansion of the implant model comprises:
calculating, for each of a plurality of points on the computational mesh, internal forces $f_{int}$, external forces $f_{ext}$, and regularizing forces $f_{reg}$;

adjusting the location of each of the plurality of points on the computational mesh based on the calculated internal forces $f_{int}$, external forces $f_{ext}$, and regularizing forces $f_{reg}$;

calculating a mean point displacement on the stent mesh based on the adjusted locations of the plurality of points on the computational mesh; and determining whether the mean point displacement on the stent mesh is less than a threshold.

12. The apparatus of claim 11, wherein calculating, for each of a plurality of points on the computational mesh, internal forces $f_{int}$, external forces $f_{ext}$, and regularizing forces $f_{reg}$ comprises:
calculating the internal forces $f_{int}$ by calculating a force $f_{angle}$ to enforce characteristic angles at strut joints of the implant model, a force $f_{length}$ to enforce strut lengths of the implant model, and a force $f_{circ}$ to enforce a circumference of the implant model.

13. The apparatus of claim 8, wherein the operations further comprise:
determining a position and an orientation for implanting the valve implant based on the simulated deployment and expansion of the implant model.

14. A non-transitory computer readable medium encoded with computer executable instructions for simulating percutaneous valve implantation, the computer executable instructions defining steps comprising:
estimating a patient-specific anatomical model of a heart valve based on 3D cardiac medical image data; and
simulating deployment of an implant model representing a valve implant into the patient-specific anatomical model of the heart valve and expansion of the implant model, wherein the implant model comprises a stent mesh that is a geometrical representation of the valve implant and a computational mesh that is a 2-simplex mesh superimposed on the stent mesh.

15. The computer readable medium of claim 14, wherein the computer executable instructions defining the step of simulating deployment of an implant model representing a valve implant into the patient-specific anatomical model of the heart valve and expansion of the implant model comprise computer executable instructions defining the steps of:
maintaining a library of implant models, each modeling geometrical properties of a corresponding valve implant; and
virtually simulating deployment and expansion of each of a plurality of the implant models maintained in the library in the patient specific anatomical model of the cardiac valve to select one of the plurality of the implant models maintained in the library for a percutaneous implantation procedure.

16. The computer readable medium of claim 14, wherein the computer executable instructions defining the step of simulating deployment of an implant model representing a valve implant into the patient-specific anatomical model of the heart valve and expansion of the implant model comprise computer executable instructions defining the step of:
simulating expansion of the implant model by balancing external forces and internal forces using an iterative optimization method.

17. The computer readable medium of claim 14, wherein the computer executable instructions defining the step of simulating deployment of an implant model representing a valve implant into the patient-specific anatomical model of the heart valve and expansion of the implant model comprise computer executable instructions defining the steps of:

(a) calculating, for each of a plurality of points on the computational mesh, internal forces $f_{int}$, external forces $f_{ext}$, and regularizing forces $f_{reg}$;
(b) adjusting the location of each of the plurality of points on the computational mesh based on the calculated internal forces $f_{int}$, external forces $f_{ext}$, and regularizing forces $f_{reg}$;
(c) calculating a mean point displacement on the stent mesh based on the adjusted locations of the plurality of points on the computational mesh; and
(d) repeating steps (a)-(c) until the mean point displacement on the stent mesh is less than a threshold.

18. The computer readable medium of claim 17, wherein the computer executable instructions defining step (a) comprise computer executable instructions defining the step of:
calculating the internal forces $f_{int}$ by calculating a force $f_{angle}$ to enforce characteristic angles at strut joints of the implant model, a force $f_{length}$ to enforce strut lengths of the implant model, and a force $f_{circ}$ to enforce a circumference of the implant model.

19. The computer readable medium of claim 14, further comprising computer executable instructions defining the step of:
determining a position and an orientation for implanting the valve implant based on the simulated deployment and expansion of the implant model.

\* \* \* \* \*